United States Patent [19]

Nichols

[11] Patent Number: 5,206,019
[45] Date of Patent: Apr. 27, 1993

[54] SOAP COMPOSITIONS CONTAINING LIQUID-LOADED POWDERS

[75] Inventor: Larry D. Nichols, Arlington, Mass.

[73] Assignee: Moleculon, Inc., Elizabeth, N.J.

[21] Appl. No.: 869,108

[22] Filed: Apr. 14, 1992

Related U.S. Application Data

[63] Continuation of Ser. No. 619,729, Nov. 29, 1990, abandoned, which is a continuation-in-part of Ser. No. 358,690, May 30, 1989, Pat. No. 5,000,947.

[51] Int. Cl.$^5$ .......................... A61K 7/02; A61K 9/14
[52] U.S. Cl. ........................................ 424/401; 424/61;
424/63; 424/65; 424/69; 424/405; 424/408;
424/409; 424/488; 424/489; 424/499;
428/402.2; 514/781; 514/844; 514/951;
252/DIG. 5; 252/106
[58] Field of Search ............... 424/405, 401, 409, 408,
424/459, 69; 252/106-108, 132, 134, DIG. 5,
DIG. 14, DIG. 16

[56] References Cited

U.S. PATENT DOCUMENTS

| | | | |
|---|---|---|---|
| 2,891,946 | 6/1959 | Volberg et al. | 260/230 |
| 3,557,083 | 1/1971 | Sacco | 260/230 |
| 3,640,741 | 2/1972 | Etes | 106/170 |
| 3,824,085 | 7/1974 | Teng et al. | 44/7 B |
| 3,940,384 | 2/1976 | Teng et al. | 260/226 |
| 3,985,298 | 10/1976 | Nichols | 428/403 X |
| 4,016,254 | 4/1977 | Seager | 424/33 |
| 4,024,073 | 5/1977 | Shimizu et al. | 252/316 |
| 4,029,726 | 6/1977 | Nichols | 264/41 |
| 4,046,717 | 9/1977 | Johnson et al. | 252/546 |
| 4,067,824 | 1/1978 | Teng et al. | 252/522 |
| 4,128,507 | 12/1978 | Mitzner | 252/522 |
| 4,193,989 | 3/1980 | Teng et al. | 424/60 |
| 4,369,173 | 1/1983 | Causland et al. | 424/35 |
| 4,383,988 | 5/1983 | Teng et al. | 424/68 |
| 4,597,960 | 7/1986 | Cohen | 424/28 |
| 4,643,856 | 2/1987 | Nichols | 264/41 |
| 4,690,786 | 9/1987 | Ninomiya et al. | 264/4.6 |
| 4,690,825 | 9/1987 | Won | 424/501 |
| 4,695,464 | 9/1987 | Aldermann | 424/449 |
| 4,708,821 | 11/1987 | Shimokawa et al. | 512/12 |
| 4,724,240 | 2/1988 | Abrutyn | 514/847 |
| 4,738,851 | 4/1988 | Schoenwald et al. | 424/488 |
| 4,752,496 | 6/1988 | Fellows et al. | 427/27 |
| 4,755,433 | 7/1988 | Patel et al. | 428/422 |
| 4,940,588 | 7/1990 | Sparks et al. | 424/489 |
| 5,000,947 | 3/1991 | Nichols | 424/69 |

OTHER PUBLICATIONS

Moleculon, Inc., Form 10-K for FY ended Nov. 30, 1988, pp. 1-7.

Primary Examiner—Thurman K. Page
Assistant Examiner—James M. Spear
Attorney, Agent, or Firm—Thomas J. Engellenner; James E. Maslow

[57] ABSTRACT

Soap compositions for topical delivery of Personal care agents are disclosed. The compositions include a soap formulation and a frangible, liquid-loaded, cellulosic powder which is blended with the soap to form the composition. The porous cellulosic powder provides a vehicle for increasing the liquid payload of a soap without diminishing its hardness or durability.

6 Claims, No Drawings

SOAP COMPOSITIONS CONTAINING LIQUID-LOADED POWDERS

REFERENCE TO RELATED APPLICATION

This application is a continuation of Ser. No. 619,729, field Nov. 29, 1990, now abandoned, which is a continuation-in-part of U.S. Ser. No. 358,690, filed May 30, 1989, now U.S. Pat. No. 5,000,947.

BACKGROUND OF THE INVENTION

The technical field of this invention is the topical application of personal care agents and, in particular, soap compositions containing personal care agents.

True soaps are typically formed by the alkaline hydrolysis of fatty esters or fatty acids in a process known as saponification. The resulting alkali metal salts are characterized by a long, oil-soluble, hydrocarbon chain attached to a water-soluble, carboxylate ion, and are particularly useful as wetting agents, emulsifying agents, and as detergents in personal care products. The term soap as used herein includes as well synthetic detergents in which the oil-soluble hydrocarbon chain is attached to a sulfate or sulfonate ion rather than to a carboxylate ion.

The ability to mix beneficial additives, such as fragrances, moisturizers and other therapeutic or desirable agents, is often limited by the tendency of such additives to degrade the physical structure of the soap. For example, fragrance and moisturizer loading for hand soaps and other shaped or compacted soap articles is typically limited to about 3 or 4 percent. At loadings above such levels, the firmness and cohesion of the soap drops off markedly.

There exists a need for better soap compositions, particularly soaps which can incorporate high loadings of liquid personal care agents.

SUMMARY OF THE INVENTION

Soap compositions for topical delivery of personal care agents are disclosed. The compositions include a soap formulation and a frangible, liquid-loaded, cellulosic powder which is blended with the soap to form the composition. These liquefiable, cellulosic powders provide a vehicle for increasing the liquid payload of a soap without diminishing its hardness or durability.

Because the liquefiable powders can be made to store up to 95 percent liquid, the liquid content of soap compositions made according to the invention can be increased to at least 8 percent without detriment to the cohesion and firmness of the soap. Moreover, the overall content of the composition can be further increased by directly blending liquid agents into the soap, achieving an overall payload content of 12 percent or higher.

Unlike most normal soap formulations, soaps containing liquid-loaded powders of the present invention primarily release their load when the composition is subjected to the normal action of washing.

Moreover, when a soap containing a powder loaded with a liquid fragrance or the like is not in use, the liquid contained in the powder can migrate from the powder into the matrix of soap until the soap is saturated and equilibrium established. As the fragrance evaporates from the surface of the soap, additional fragrance can migrate from the powder to maintain equilibrium. In this way, the fragrance of a soap can be maintained for a much longer period than with conventional formulations.

Hand and toilet soaps, for example, can be formed by a saponific reaction of sodium hydroxide with a mixture of tallow, palm oil and coconut oil. The resulting product can be shredded and partially dried. Frangible, liquid-loaded, cellulosic powders (e.g., containing fragrances, moisturizers or the like) can then be mixed into the soap by milling and the mixed product can then be pressed into cakes. Soaps, according to the present invention, can also include salts, fatty acids, air, whitening agents, synthetic detergents, phosphates, emulsifiers, surfactants, emollients, and moisturizing agents either encapsulated within the cellulosic particles or incorporated into the soap matrix.

Soap formulations useful in the present invention can include, for example, sodium isethionate, sodium cocoyl isethionate, sodium stearate, sodium tallowate, sodium palm kernate, sodium cocoate, and sodium dodecylbenzenesulfonate, as well as fatty acids, such as stearic acid and coconut acid, together with other additives, such as sodium chloride, titanium dioxide, trisodium EDTA and the like.

In one technique, the liquefiable powders are formed by dissolving a cellulosic polymer and a pore-forming liquid in a volatile, polar solvent (e.g., a low molecular weight halogenated hydrocarbon, ester or diester) and then dispersively evaporating the solution, for example, by spray drying. Suitable volatile solvents for cellulosic polymers include methylene chloride, acetone, ethyl acetate, ethyl carbonate, methyl formate and the like. Methylene chloride is a preferred solvent when the cellulosic polymer is cellulose triacetate. Alternatively, other volatile solvents, such as formic acid or the like, can be used, and the resulting solution can be sprayed into a non-solvent, such as methanol, where the powder particles are then recovered by filtration and rinsing. The active agent can be incorporated into the solvent or introduced by liquid phase substitution after the powder is formed.

The cellulosic powder particles useful in the present invention can range from about 1 to about 500 micrometers in average diameter, preferably from about 5 to about 100 micrometers in average diameter, and typically are roughly microspherical in shape. They are further characterized by being microporous with interconnecting pores ranging in size from about 1 to about 500 nanometers and capable of holding liquid payloads of active agents. The cellulosic powder can be formed from cellulosic polymers chosen from the group of cellulose acetates, cellulose butyrates, cellulose nitrates, cellulose propionates, ethyl celluloses and discrete or molecular mixtures thereof. One preferred cellulosic powder is a polymeric powder of cellulose triacetate having a (dry) acetyl content greater than about 42 percent. The liquid content of the cellulosic powders of the present invention can range from about 50 percent to about 95 percent by weight.

In addition to fragrances and moisturizers, the liquid-loaded, cellulosic powders of the present invention can further encompass a wide variety of personal care agents, including oils, deodorants, antiperspirants, emollients, lubricants, colorants, insect repellents, analgesics, pore cleansing agents, antibacterial agents, fungicides, foot and acne preparations and other skin medications.

In some applications, it may also be preferable to include a quantity of a dry cellulosic powder (e.g., less than 50 percent of the total cellulosic components) to provide additional structural integrity to the composition. The term "dry cellulosic Powder" is used herein to describe powders whose internal pores are liquid-free or have a liquid content of less than 50 percent.

Further details on the formation of liquid-loaded and dry powders can be found in the above-referenced parent application, U.S. Ser. No. 358,690 filed May 30, 1989, now U.S. Pat. No. 5,000,947, and commonly-owned, copending application entitled "Process For Producing Liquid-Loaded Powders" by Larry D. Nichols and John F. Cline filed on even date herewith, both of which are incorporated herein by reference.

The invention will next be described in connection with certain exemplary methods and compositions. However, it should be clear that various additions, subtractions and changes can be made without departing from the spirit or scope of the invention.

DETAILED DESCRIPTION

The example below illustrates the preparation of soap compositions contained liquefiable powders.

EXAMPLE 1

A commercial blend of natural soap stick containing sodium tallowate and sodium cocoate in a 80:20 ratio was milled and ground several times to produce a dough. The mixture was put through an auger and extruded several times during which 4 percent of pure perfume oil was added, along with 2.5 percent of a cellulosic powder previously produced containing 80 percent perfume oil as the active ingredient, for a total perfume oil content of 6 percent. The extrudate was put into a long bar mold, and when solidified, was chopped into small bars.

The resulting moderately fragrant bars were firm to the touch and showed almost no indentation when pressed firmly with a fingertip.

EXAMPLE 2

Sample bars of soap were prepared by the method of Example 1 but using 4 percent pure perfume oil plus 5 percent of cellulosic powder containing 80 percent perfume oil, for a total perfume oil content of 8 percent.

The resulting bars were highly fragrant, slightly soft to the touch, and showed only a slight indentation when firmly pressed with a fingertip.

EXAMPLE 3

An attempt was made to prepare bars of soap according to the method of Example 1 but using 6 percent of pure perfume oil and no cellulosic powder.

The molded material did not fully congeal, but remained a soft mass which could readily be penetrated by fingertip pressure.

What is claimed is:

1. A soap composition for the delivery of a personal care agent during washing, the composition comprising a soap formulation and a frangible, liquid-containing, cellulosic powder formed by spray evaporation and having particles ranging in average diameter from about 1 to about 500 micrometers, the particles being microporous with a plurality of interconnecting pores ranging in size from about 1 to about 500 nonometers and having a liquid personal care agent loaded within the pores, such that the composition has a liquid content ranging from about 50 percent to about 95 percent by weight and upon washing use of the soap, the loaded pores readily release their load.

2. the composition of claim 1 wherein the cellulosic powder is a polymeric powder chosen from the group consisting of cellulose acetates, cellulose butyrates, cellulose nitrates, cellulose propionates, ethyl celluloses, and discrete and molecular mixtures thereof.

3. The composition of claim 1 wherein the personal care agent is incorporated into a liquid phase within the particles.

4. The composition of claim 1 wherein the personal care agent is chosen from the group consisting essentially of fragrances, moisturizers, oils, emollients, lubricants, colorants, deodorants, antiperspirants, insecticides, fungicides, antibacterial agents, foot care preparations, acne preparations, pore cleansing agents, and analgesics.

5. The composition of claim 1 wherein the composition further comprises a personal care agent not incorporated within the frangible powder.

6. The composition of claim 1 wherein the composition further comprises a dry, cellulosic powder also blended into the soap in order to provide additional structural integrity to the composition.

* * * * *

UNITED STATES PATENT AND TRADEMARK OFFICE
CERTIFICATE OF CORRECTION

PATENT NO.   :   5,206,019
DATED        :   April 27, 1993
INVENTOR(S)  :   Larry D. Nichols It is certified that error appears in the above-identified patent and that said Letters Patent is hereby corrected as shown below:

On the title page:

[73] Assignee reads:

--PurePac, Inc., Elizabeth, N.J.--

Signed and Sealed this

Eleventh Day of January, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,206,019
DATED : April 27, 1993
INVENTOR(S) : Larry D. Nichols

It is certified that error appears in the above-identified patent and that said Letters Patent is hereby corrected as shown below:
On the Title Page:

Please amend the above-referenced patent so that Page 1, [73] Assignee reads:

--PUREPAC, INC. Elizabeth, N.J.--

This certificate supersedes Certificate of Correction issued Jan. 11, 1994.

Signed and Sealed this

Second Day of August, 1994

Attest:

BRUCE LEHMAN

Attesting Officer

Commissioner of Patents and Trademarks